United States Patent [19]

Wiegel

[11] Patent Number: 5,769,786
[45] Date of Patent: Jun. 23, 1998

[54] CATHETER SET WITH AN ECG CONTACT CAPABILILTY

[75] Inventor: Heinz Wiegel, Alheim, Germany

[73] Assignee: B. Braun Melsungen AG, Melsungen, Germany

[21] Appl. No.: 778,554

[22] Filed: Jan. 3, 1997

[30] Foreign Application Priority Data

Jan. 26, 1996 [DE] Germany .................. 296 01 310 U

[51] Int. Cl.⁶ ...................................................... A61B 5/00
[52] U.S. Cl. .......................... 600/372; 600/373; 600/374; 600/381; 600/585
[58] Field of Search .................................. 128/642, 772; 607/116, 119, 122; 439/828, 829, 909; 600/373, 372, 374, 381, 585

[56] References Cited

U.S. PATENT DOCUMENTS

| | | |
|---|---|---|
| 4,369,794 | 1/1983 | Farler ...................................... 128/642 |
| 4,874,376 | 10/1989 | Hawkins, Jr. ............................ 128/772 |
| 5,170,787 | 12/1992 | Lindegren ............................... 128/772 |
| 5,186,179 | 2/1993 | MacEachern ........................... 128/772 |
| 5,243,995 | 9/1993 | Maier . | |

FOREIGN PATENT DOCUMENTS

| | | |
|---|---|---|
| 486979 | 10/1995 | European Pat. Off. . |
| 4319033 | 6/1993 | Germany . |

*Primary Examiner*—Jennifer Bahr
*Assistant Examiner*—David M. Ruddy
*Attorney, Agent, or Firm*—Akin, Gump, Strauss, Hauer & Feld LLP

[57] ABSTRACT

A catheter set includes a flexible catheter which is placed over a guide wire according to the Seldinger technique. A clamp is provided which can be laterally applied to the guide wire for tapping electrical potential from the guide wire. The clamp is laterally applied and directly attached to the proximal end of the guide wire when the distal portion of the guide wire is surrounded by the catheter and the tip of the guide wire protrudes from the catheter tip.

8 Claims, 3 Drawing Sheets

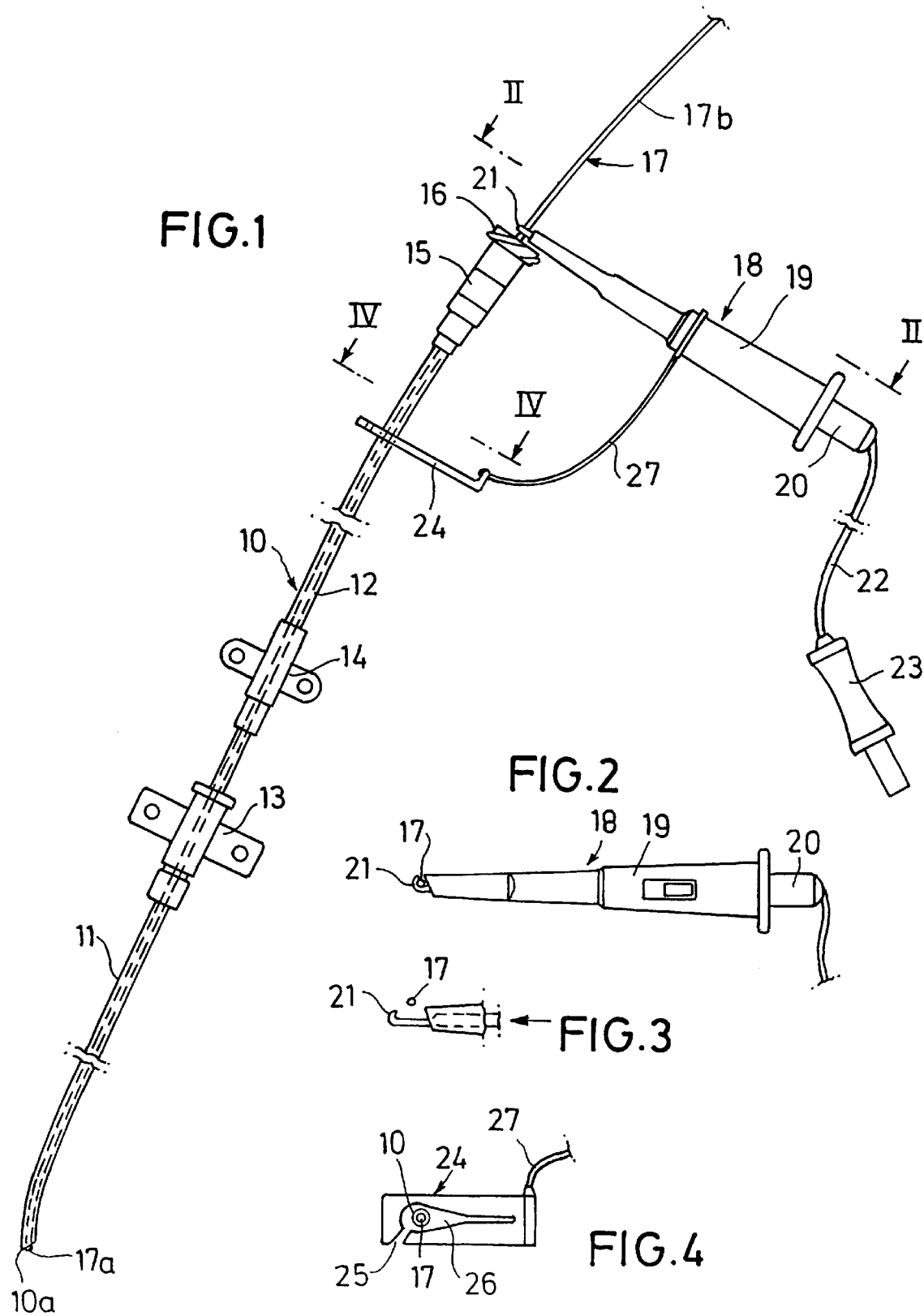

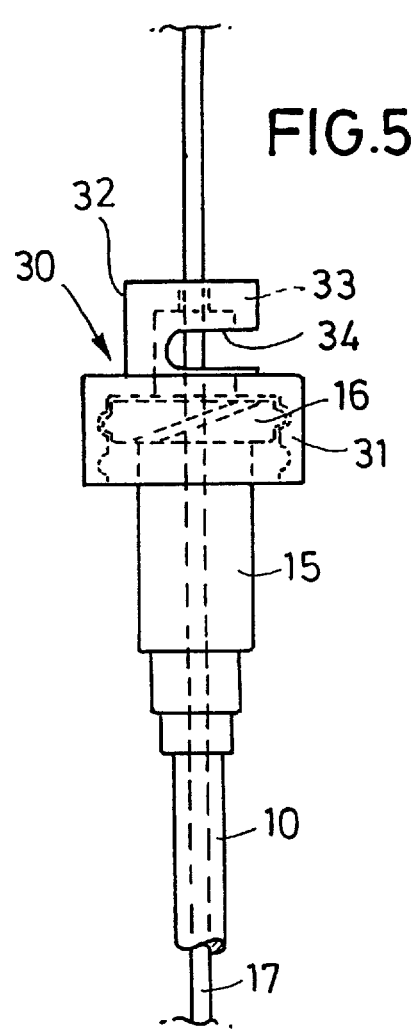
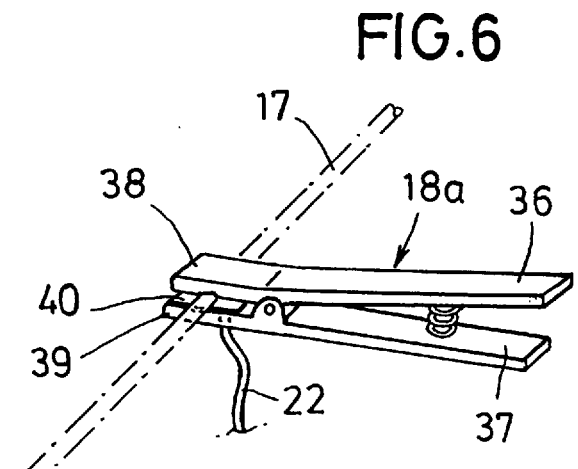
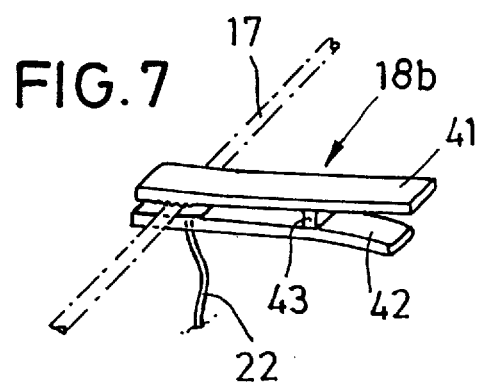
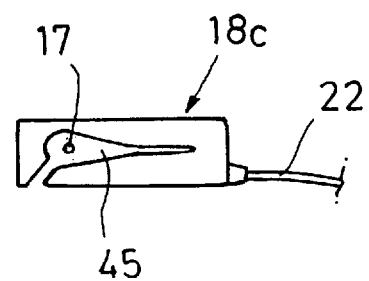

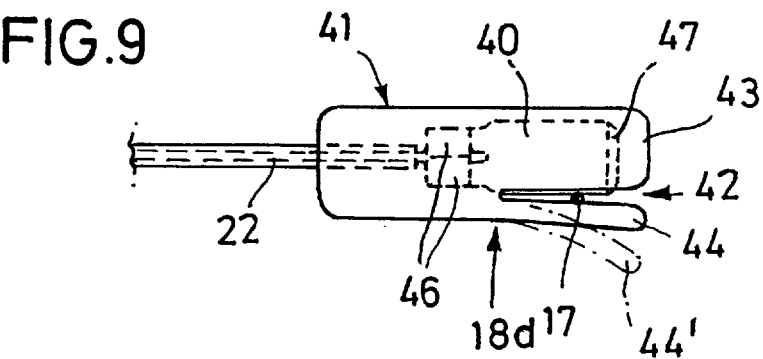
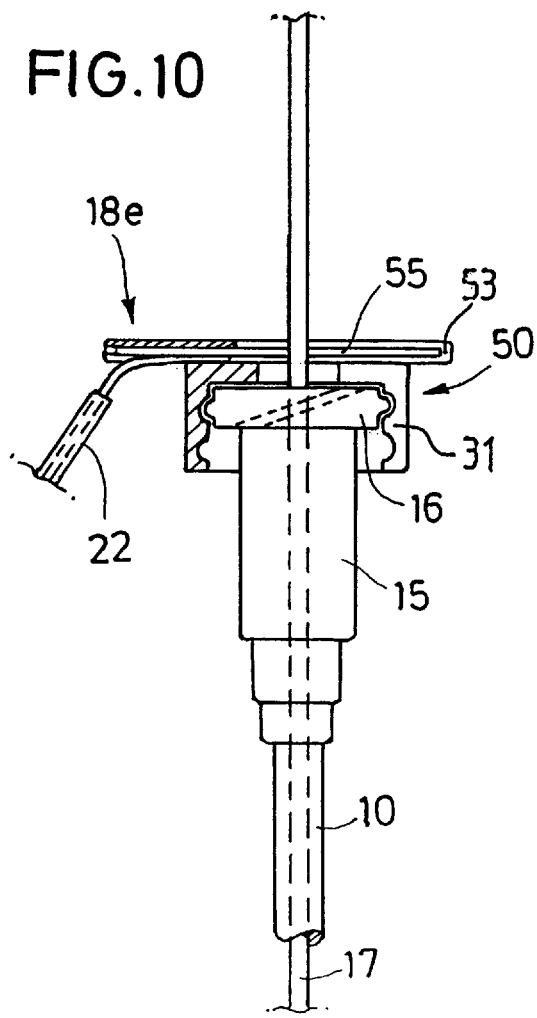
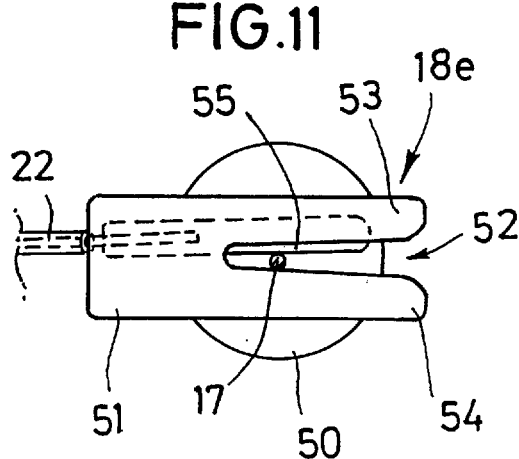

CATHETER SET WITH AN ECG CONTACT CAPABILILTY

BACKGROUND OF THE INVENTION

The invention relates to a catheter set with an ECG (electrocardiogram) contact capability, comprising a flexible catheter and an electrically conductive guide wire over which the catheter can be slipped.

From European Patent 0 486 979, a catheter set with an ECG contact capability is known, wherein the catheter can be slipped over a guide wire inserted in the patient body until the catheter tip has reached the target region. With a puncture cannula, the guide wire is inserted into the vena cava leading to the right atrium of the heart. The guide wire is connected to an electrocardiograph by which the respective position of the guide wire tip can be detected. Thus, it can be detected, without X-ray survey, whether the catheter tip has reached its target or not. According to another technique, the ECG branching from the guide wire is made only when the guide wire has been pushed up to the target and the catheter has been slipped onto the guide wire thereafter, with their tips being flush with each other. As soon as the ECG graph indicates the correct placement of the catheter tip, the guide wire is withdrawn from the catheter. For the ECG branching, a clamping bushing is provided which is applied onto the proximal (patient-distal) end of the guide wire and comprises a connection piece for a plug device connected to the electrocardiograph. Thus, the connector is arranged at the proximal end of the guide wire. Because of the weight of the connector and the plug device mounted thereto, the end of the guide wire is "top-heavy", whereby the guide wire tends to be retracted into the catheter and change its position. Moreover, the connector mounted to the catheter end can prove to be disadvantageously disturbing for the handling of the catheter set. After the catheter has been slipped over the guide wire, it is finally also required to mount the connector at the end of the guide wire which is arranged at some distance to the proximal catheter end. In the course of this, the physician has to perform manipulations at different sites of the catheter set.

From German Patent 43 19 033, there is further known a catheter set in which the connector for the electrical connection of the guide wire is arranged in a bushing which can be slipped over the guide wire and mounted to the catheter hub. Although the connector does not load the guide wire here, it is necessary to slip the bushing from the proximal end over a considerable length of the guide wire.

SUMMARY OF THE INVENTION

It is the object of the present invention to provide a catheter set with an ECG contact capability which permits a simpler attachment of the connector to the guide wire.

In the catheter set according to the invention, the connector consists of a clamp which can be laterally applied to the guide wire. This has the advantage that the connector can be laterally slipped onto the guide wire directly behind the catheter hub and does not have to be slipped over the guide wire from the proximal end. In the course of this, the physician can concentrate on the region of the catheter hub during his manipulations. As soon as the catheter has been pushed to the guide wire such that their tips are flush, the clamp can be laterally clamped onto the guide wire directly behind the catheter hub. This simultaneously prevents an unintentional advancement of the guide wire in the interior of the catheter.

The catheter set according to the invention is particularly suitable for making ECG branchings after the catheter has been placed, a fine positioning of catheter and guide wire being possible from the ECG graph. Generally, the clamp can be applied at all points of the guide wire if the latter is bare, i.e., not insulated. It is also possible to initially place an insulated guide wire under ECG survey, subsequently remove the clamp and then slip the catheter over the guide wire. At one or more designated contact points, the insulation of the insulated guide wire is interrupted for the attachment of the clamp. A third possibility consists in that the clamp comprises a mandril penetrating the insulation of the guide wire and establishing an electrical contact with the wire core while the clamp is slipped onto the guide wire.

The clamp may comprise two clamping portions which are manually movable relative to each other, clamp the guide wire between themselves, consist of a substantially rigid electrically conductive sliding clamp with a laterally open clamping gap, or consist of two clamping arms integrally and elastically interconnected, one clamping arm comprising an electrically conductive clamping jaw.

In a preferred further embodiment of the invention, a holding member is provided which secures the clamp engaging the guide wire directly behind the catheter hub against axial displacement relative to the catheter hub. The clamp engages with the holding member in such a manner that it can no longer be displaced relative to the catheter hub. Since the clamp itself is clamped at the guide wire, a securing of the axial position of the guide wire with respect to the catheter is achieved through the holding member. This means that the guide wire can neither be moved forward nor rearward within the catheter.

BRIEF DESCRIPTION OF THE DRAWINGS

Hereinafter, embodiments of the invention are described in detail with respect to the drawings, in which:

FIG. 1 is an illustration of the catheter set in the state of being placed during the ECG branching, FIG. 2 is a side view of the clamp used in FIG. 1 in the clamping state, FIG. 3 shows the tip of the clamp in the released state, FIG. 4 shows the sliding clamp for the mutual fixing of the positions of guide wire and catheter, FIG. 5 shows a holding member mounted to the catheter hub, through which the clamp can engage, FIG. 6 shows a further embodiment of the clamp, FIG. 7 shows a third embodiment of the clamp, FIG. 8 shows a clamp in the form of an electrically conductive rigid sliding clamp, FIG. 9 shows a fourth embodiment of the clamp with spreadable clamping slot legs, FIG. 10 shows a fifth embodiment of the clamp with a holding member mounted to the catheter hub, and FIG. 11 is a plan view of the clamp of FIG. 10.

DESCRIPTION OF THE PREFERRED EMBODIMENTS

The catheter set illustrated in FIG. 1 comprises a catheter 10 which here consists of an intracorporal first catheter section 11 and an extracorporal second catheter section 12. The catheter section 11 is introduced into the patient body, and it consists of a physically compatible soft plastic material. The second catheter section remains outside the patient body. It consists of transparent plastic and permits to view the catheter interior to observe the guide wire and/or a liquid in the catheter interior.

A fixing device 13, which is displaceable and serves to fix the proximal end of the catheter section 11 at the skin of the patient, is seated on the first catheter section 11. A further fixing device 14 is provided at the transition between the first catheter section 11 and the second catheter section 12.

A conventional catheter hub 15 mounted to the end of the catheter section 12 is located at the proximal end of the catheter 10. The catheter hub 15 comprises an inner cone and is externally provided with a Lock connector 16 permitting the connection of a syringe or a hose coupling to the catheter.

The guide wire 17, which can be inserted into the catheter 10, forms part of the catheter set. In the state of being placed, the tip 17a is flush with the catheter tip 10a, whereas the rear section 17b projects from the catheter hub 15 at the proximal end by a length of about 20 to 30 cm. Hence, the guide wire 17 is considerably longer than the catheter 10. It comprises a marking which, when the tips of catheter and guide wire are even, is just visible at the rear end of the catheter hub.

In this embodiment, the guide wire 17 consists of a stranded or helically wound bare wire, which has a certain flexibility and a linear configuration. The tip section near the tip 17a is bent in the shape of a U and softer than the remaining portion, which, however, cannot be seen in FIG. 1 because the catheter holds the tip portion in a stretched state there.

The catheter 10 is placed according to the Seldinger technique, according to which the vein is first punctured by a puncture cannula (not shown), and then the guide wire 17 is advanced into the vein up to the target region of the catheter through the puncture cannula. After the puncture cannula has been withdrawn, the guide wire remains in the patient body. Then, the catheter is slipped over the guide wire 17 until the catheter tip 10a is flush with the tip 17a of the guide wire 17. The fact that the tip has reached its correct position can be detected from a marking which is provided on the guide wire 17 and located directly behind the catheter hub 15 after the tip evenness has been established. For branching off the ECG signal from the guide wire 17, the clamp 18 is laterally applied to the guide wire 17. In this embodiment, the clamp 18 is an electric potential clamp comprising an elongate body 19 of plastic material in which a spring-loaded slide 20 protruding from the rear end is arranged, which is connected to a contact finger 21 advanceable out of the front end. This contact finger 21 is connected to a cable 22 whose plug 23 can be connected to the electrocardiograph (not shown). The cable 22 leads out of the projecting end of the slide 20. In order to mount the clamp 18 to the guide wire 17, the holder 19 is held between index and middle fingers, while the thumb axially presses against the spring-loaded slide 20. Thereby, the contact finger 21 bent in a hook-like manner is axially advanced (FIG. 3) so that it can embrace the guide wire 17. When the slide 20 is released, the contact finger 21 is pulled against the body 19, clamping the guide wire 17, as is shown in FIG. 2. This creates a secure contact between the contact finger 21 and the guide wire 17. The clamping is so strong that displacements of the contact finger 21 along the guide wire 17 are prevented.

Further, according to FIG. 1, a sliding clamp 24 made of plastic is provided, which is illustrated in FIG. 4. This sliding clamp 24 comprises a lateral introducing slot 25 leading into a wedge-shaped clamping opening 26. The sliding clamp 24 is made of an elastic plastic material. It is laterally slipped over the catheter section 12 having the guide wire 17 arranged therein, so that the catheter 10 comes into the region of the wedge opening 26. By laterally displacing the sliding clamp 24, the catheter 10 is clamped in the wedge opening 26 and pressed against the guide wire 17, whereby the guide wire is secured against axial displacement in the catheter. The sliding clamp 24 is connected to the clamp 18 by means of a band 27, so that it cannot get lost or fall down.

In the embodiment of FIG. 5, additional provision is made of a holding member 30 which can be mounted to the catheter hub 15. This holding member 30 consists of a Lock nut 31 which can be screwed onto the Lock connector 16, and an extension 32 axially projecting therefrom and comprising a lateral slot 33 and a radial recess 34. The slot 33, which also extends through the Lock nut 31 and thus over the entire length of the holding member 30, serves to be able to laterally slip the holding member over the guide wire 17 before the holding member is screwed onto the Lock connector 16. Through the opening 34, the clamp 18 is applied to the guide wire 17. The holding member 18 makes the sliding clamp 24 dispensable. It also fixes the clamp 18 applied to the guide wire in the proximal direction so that the guide wire 17 is immobilized in the catheter 10 via the clamp.

FIG. 6 shows another embodiment of the clamp 18a which here is configured in the manner of a clothes-peg and comprises two hinged clamp legs 36,37 which are pressed apart by a spring, whereby clamping jaws 38,39 enclosing the guide wire 17 are pressed against each other. One of the clamping jaws is provided with a contact piece 40 connected to a cable 22 leading to the electrocardiograph.

A similar clamp 18b is illustrated in FIG. 7. Here, the clamping jaws 41,42 are integrally formed with an elastic plastic bending web 43 which effects that the clamping jaws are pressed against each other. By pressing the clamp legs against each other, the clamp can be opened.

FIG. 8 shows a clamp 18c in the form of a one-piece sliding clamp comprising a laterally open clamping gap 45 and consisting of electrically conductive material. The sliding clamp has a form similar to that of the sliding clamp 24 of FIGS. 1 and 4. It only serves, however, to clamp the guide wire 17 which it thus electrically connects to the cable 22.

FIG. 9 shows another embodiment of a clamp 18d. The clamp 18d substantially consists of a metal contact sheet 40 to which the cable 22 is mounted and which is cast in a housing block 41 made of a non-conductive plastic material. The integral housing block 41 comprises a slot 42 separating two clamping arms 43,44 of the housing block 41. The two clamping arms 43,44 are elastically interconnected via the housing body. The narrower clamping arm 44 can be bent away from the broader clamping arm 43 into a spread position 44' so that the slot 42 becomes broader and assumes a V-shape.

The metal contact sheet 40 is cast into the housing block 41 such that a longitudinal edge of the metal contact sheet 40 projects from the larger clamping arm 43 toward the inside of the slot.

At the end of the housing block 41 facing away from the slot 42, the wire core of the cable 22 is electrically and mechanically connected to the metal contact sheet 40 by two clamping tongues 46 of the metal contact sheet 40.

The clamp 18d is slipped onto the guide wire 17 by manually spreading the narrower clamping arm 44 away from the broader clamping arm 43. In this state, the clamp 18d is slipped onto the guide wire 17 with its V-shaped opened slot 42. Finally, when the narrower clamping arm 44 is released again, it clamps the guide wire 17 in the slot 42 which is now tight and narrow again. In doing so, the guide wire 17 is pressed against the metal contact sheet 40, whereby a secure electrical contact between the guide wire 17 and the metal contact sheet 40 is ensured. The clamp 18d of this configuration can be mounted to the guide wire 17 without displacing or twisting the latter.

The front end 47 of the metal contact sheet 40 is chamfered toward all sides. The chamfering at the side facing the slot 42 effects that the metal contact sheet 40 cannot be caught at the guide wire 17 when the clamp 18d is slipped on, but that the guide wire 17 is guided into the slot 42 along the chamfering.

FIGS. 10 and 11 show a further embodiment, wherein a clamp 18e is part of the holding member 50 which is screwed onto the Lock connector 16 shown in FIG. 5. The clamping portion 51 is adhered to a slitted Lock nut 50 already shown in FIG. 5 as well. The clamping portion 51 comprises a slot 52 separating two identical clamping arms 53,54 and being aligned with the slot 31 of the Lock nut 50. In one clamping arm 54, a metal contact sheet 55 is embedded which protrudes from the clamping arm 54 toward the slot inside. The cable 22 is electrically and mechanically connected to the metal contact sheet 55 by soldering.

In order to tap electrical signals from the guide wire 17, the clamp 18e is laterally slipped over the guide wire 17. In doing so, the guide wire 17 is pushed into the slots 31,52 of the Lock nut 50 and clamping portion 51, whereupon the Lock nut 50 is screwed onto the Lock connector 16. In the course of this, the guide wire 17 is threaded further into the slot 52 so that the guide wire 17 is firmly pressed against the metal contact sheet 55 and a good electrical contact between the guide wire 17, the metal contact sheet 55 and the cable 22 is effected.

What is claimed is:

1. A catheter set with an ECG contact capability, comprising:
   a flexible catheter having a catheter tip at its distal end and a catheter hub at its proximal end,
   a guide wire over which the catheter can be slipped, the guide wire having a proximal end, a distal portion, and a tip, and
   a connector for tapping electrical potential of the guide wire and adapted to be attached to the guide wire, the connector comprising a clamp adapted to be laterally applied and directly attached to the proximal end of the guide wire when the distal portion of the guide wire is surrounded by the catheter and the tip of the guide wire protrudes from the catheter tip.

2. The catheter set according to claim 1, wherein the clamp comprises two clamping portions manually moveable relative to each other, which clamp the guide wire therebetween.

3. The catheter set according to claim 1, wherein the clamp comprises a substantially rigid, electrically conductive sliding clamp having a laterally open clamping gap.

4. The catheter set according to claim 1, wherein the clamp comprises two integrally formed clamping arms which are elastically interconnected, one of the clamping arms comprising an electrically conductive clamping jaw.

5. A catheter set with an ECG contact capability, comprising:
   a flexible catheter having a catheter hub at its proximal end,
   a guide wire over which the catheter can be slipped, and
   a connector for tapping a electrical potential of the guide wire and adapted to be attached to the guide wire,
   wherein the connector comprises a clamp adapted to be laterally applied to the guide wire, and
   wherein a sliding clamp is provided, fixing the catheter and the guide wire located therein relative to each other, and wherein the sliding clamp is undetachably connected to the clamp.

6. A catheter set with an ECG contact capability, comprising:
   a flexible catheter having a catheter hub at its proximal end,
   a guide wire over which the catheter can be slipped, and
   a connector for tapping electrical potential of the guide wire and adapted to be attached to the guide wire,
   wherein the connector comprises a clamp adapted to be laterally applied to the guide wire and,
   further comprising a holding member mounted on the catheter hub for securing the clamp to engage the guide wire directly behind the catheter hub for preventing axial displacement of the guide wire relative to the catheter hub.

7. The catheter set according to claim 6, wherein the holding member is a Lock nut to be screwed onto the catheter hub and further including a longitudinally extending slot for being laterally slipped over the guide wire.

8. The catheter set according to claim 6 or 7 comprising a holding member, wherein the clamp comprises a part of the holding member.

* * * * *